US00PP15292P2

(12) United States Plant Patent
Thomas et al.

(10) Patent No.: US PP15,292 P2
(45) Date of Patent: Nov. 2, 2004

(54) ***EUPHORBIA* PLANT NAMED 'FIRST BLUSH'**

(50) Latin Name: *Euphorbia epithymoides*
Varietal Denomination: First Blush

(76) Inventors: Liesl Thomas, W168 N12276 Century La., Germantown, WI (US) 53022; George Radtke, W168 N12276 Century La., Germantown, WI (US) 53022

( * ) Notice: Subject to any disclaimer, the term of this patent is extended or adjusted under 35 U.S.C. 154(b) by 1 day.

(21) Appl. No.: 10/601,744

(22) Filed: Jun. 23, 2003

(51) Int. Cl.[7] ..... A01H 5/00
(52) U.S. Cl. ..... Plt./302
(58) Field of Search ..... Plt./302

*Primary Examiner*—Kent Bell

(57) ABSTRACT

A new cultivar of *Euphorbia* named 'First Blush' that is distinguished by a compact clumping habit, winter dormancy, showy variegated pale green foliage with rose colored tints, and yellow flowers in spring. In combination these traits set 'First Blush' apart from all other existing varieties of *Euphorbia* known to the inventor.

2 Drawing Sheets

Genus: *Euphorbia.*
Species: *epithymoides.*
Denomination: First Blush.

BACKGROUND OF THE INVENTION

The present invention relates to a new and distinct cultivar of variegated cushion spurge, a hardy perennial that is grown for use as an ornamental shrub for the landscape. The new invention is known botanically as *Euphorbia* and will be referred to hereinafter by the cultivar name 'First Blush'.

'First Blush' is a sport that was discovered by the inventor in 1996 in a cultivated area of Germantown, Wis. 'First Blush' was discovered as a variegated branch on an unnamed individual plant of *Euphorbia epithymoides* among a production block grown from seed. 'First Blush' was selected by the inventor based on its variegated foliage and variegated bracts. The foliage is pale green with cream-white margins. In spring the upper foliage nearest the sun is tilted rose-pink and then turns a more pronounced rose-red color in fall. Whorls of bracts are pale green with cream-white margins on stems that are often tinted red. 'First Blush' exhibits low vigor resulting in a less invasive plant than the species. The variegation makes 'First Blush' a showier variety than other *Euphorbia* known to the inventor.

The first asexual reproduction of 'First Blush' was carried out in a cultivated area of Germantown, Wis. by the inventor. The method used was stem cuttings. Since that time subsequent generations have been determined stable and true to type.

SUMMARY OF THE INVENTION

The following traits have been repeatedly observed and represent the distinguishing characteristics of the new *Euphorbia* cultivar 'First Blush'. These traits in combination distinguish 'First Blush' from all other existing varieties of *Euphorbia* known to the inventor. 'First Blush' has not been tested under all possible conditions and phenotypic differences may be observed with variations in environmental, climatic, and cultural conditions, however, without any variance in genotype.

1. *Euphorbia* 'First Blush' exhibits a compact, clumping habit.

2. *Euphorbia* 'First Blush' exhibits variegated foliage with pale green centers and cream-white margins with slightly crinkled edges.
3. *Euphorbia* 'First Blush' exhibits whorls of variegated pale green and cream-white bracts.
4. *The edges of the upper foliage on Euphorbia* 'First Blush' turn rose-pink in spring and deepen in color to rose-red in fall.
5. *Euphorbia* 'First Blush' exhibits low vigor and is less invasive than the species.
6. *Euphorbia* 'First Blush' is hardy to USDA Zone 4b.
7. *Euphorbia* 'First Blush' is winter dormant.
8. *Euphorbia* 'First Blush' exhibits yellow flowers in spring.

BRIEF DESCRIPTION OF THE DRAWINGS

The accompanying drawings illustrate the distinguishing traits of the new *Euphorbia* cultivar 'First Blush'. The drawings were made in spring and summer of plants grown out-of-doors in a cultivated area of Germantown, Wis. The plants were in one-liter containers at the time.

The drawing on sheet 1 illustrates the variegated foliage with rose-pink edges.

The drawing on sheet 2 illustrates the plant in bloom. The drawings were made using conventional techniques and although flower and foliage colors may appear different from actual colors due to light reflectance, they are as accurate as possible by conventional photography.

BOTANICAL DESCRIPTION OF THE PLANT

The following is a detailed botanical description of the new *Euphorbia* cultivar 'First Blush'. Observations, measurements, values and comparisons were collected in Arroyo Grande, Calif. from plants grown out-of-doors in one-liter containers. The observed plants were approximately nine to ten months old. The botanical data was collected as the plants grew back and matured after winter die-down, the plants having been started as cuttings in the late summer of the previous year. Color determinations are made in accordance with The 2001 Royal Horticultural Society Colour Chart from London England, except where general color terms of ordinary dictionary significance are used.

Botanical classification: *Euphorbia* 'First Blush'.
Species: *epithymoides.*
Common name: Variegated cushion spurge.
Parentage: *Euphorbia* 'First Blush' is a sport of the following parent plant:
*Parent plant.*—An individual unnamed plant of *Euphorbia epithymoides.*
Propagation method: Division and cuttings.
Rooting habit: Fibrous.
Time to develop roots: 2–3 weeks are needed for initial cuttings to develop roots.
Crop time: 8–12 months are needed to produce a one-liter container from a rooted cutting.
Growth habit: Compact, clumping habit.
Use: Ornamental shrub for rock gardens and perennial borders.
Type: Perennial.
Height of plant: 18 cm. in height in a one-liter container.
Width of plant: 27 cm. in width in a one-liter container.
Cultural requirements: Plant in well-draining soil and full sunlight with moderate water. Needs filtered shade in hot climates.
Hardiness: Hardy to USDA Zone 4b.
Seasonal traits: Yellow flowering in spring and rose tinted foliage from spring to fall.
Toxicity: When cut or bruised plant exudes milky white latex that can be toxic and may elicit dermal irritation.
Disease and pest resistance and susceptibility: Not resistant nor particularly susceptible to any diseases or pests known to the inventor.
Stem:
*Branching habit.*—Basal branching.
*Internode dimensions.*—5 mm. between nodes.
*Stem color.*—A combination of 138B and 61A.
*Stem shape.*—Cylindrical.
*Stem diameter.*—3 mm. in diameter.
*Stem length.*—12 cm. in length.
*Stem surface.*—Heavily pubescent.
*Color of pubescence.*—156D.
Foliage:
*Type.*—Deciduous.
*Leaf arrangement.*—Spiral.
*Leaf division.*—Simple.
*Leaf shape.*—Oblong elliptic.
*Leaf length.*—2 cm. in length.
*Leaf width.*—1 cm. in width.
*Leaf apex.*—Acute.
*Leaf base.*—Rounded.
*Leaf venation pattern.*—Visible mid-vein.
*Vein color.*—138D.
*Margin.*—Entire and revolute.
*Leaf surface* (*abaxial surface*).—Pubescent.
*Leaf surface* (*adaxial surface*).—Pubescent.
*Leaf texture.*—Slightly crisped.
*Leaf attachment.*—Petiole.
*Petiole dimensions.*—2.50 cm. in length and 1.25 mm. in width.
*Petiole color.*—138B.
*Petiole surface.*—Glabrous.
*Leaf color in spring* (*adaxial and abaxial surface*).—Centers are N138D and margins are 158B with edges tinted 63C.
*Leaf color in fall* (*adaxial and abaxial surface*).—Centers are N138D and margins are 158B with edges tinted 58A.
Bracts:
*Bract color* (*adaxial surface*).—Center is N138D, margin is 158C and edge is 67A.
*Bract color* (*abaxial surface*).—Center is 138C, margin is 158D and edge is 67D.
*Number of bracts.*—Approximately 17 in number.
*Bract arrangement.*—Whorled.
*Fused or unfused.*—Unfused.
*Bract dimensions.*—Range in size from 1.50 mm. in length to 6 mm. in length and 1.25 mm. in width to 5 mm. in width.
*Bract surfaces* (*adaxial and abaxial surfaces*).—Pubescent.
*Bract shape.*—Oblong.
*Bract apex.*—Acute.
*Bract base.*—Rounded.
*Bract margins.*—Entire.
Cyathia:
*Arrangement.*—Terminal cyathium.
*Number of cyathia.*—A range of 25–30 cyathium per 1-liter container.
*Dimensions of cyathia.*—4 mm. in height and 6 mm. in width.
*Cyathia color* (*adaxial and adaxial surfaces*).—Colors 11C, 138A, and 63C are individually present.
*Petals.*—Apetalous.
*Sepals.*—Asepalous.
*Flowering season.*—Mid spring to summer.
*Lastingness of flower on plant.*—5–10 days.
*Flower aspect.*—Facing upward.
*Fragrance.*—Absent.
*Peduncle color.*—138B.
*Peduncle length.*—1 cm. in length.
*Peduncle width.*—1 mm. in width.
*Peduncle shape.*—Cylindrical.
*Peduncle surface.*—Glabrous.
*Shape of petaloid appendages.*—Oblong elliptic.
*Color of petaloid appendages.*—11A.
*Dimensions of petaloid appendages.*—7 mm. in width and 14 mm. in length.
*Petaloid appendage surface* (*adaxial and abaxial surfaces*).—Glabrous.
*Number of petaloid appendages.*—Six in number.
*Petaloid appendage margins.*—Entire and sinuate.
*Petaloid appendage apex.*—Rounded.
*Petaloid appendage base.*—Attenuate.
Reproductive organs:
*Stamen.*—Six in number.
*Stamen color.*—161A.
*Stamen length.*—1 mm. in length.
*Stamen form.*—Jointed filament.
*Anther color.*—161A.
*Anther dimensions.*—0.25 mm. in width and 0.25 mm. in length.
*Pollen amount.*—Low amount.
*Pollen color.*—161A.
*Pistil.*—One in number.
*Pistil length.*—1.50 mm. in length.
*Pistil color.*—11A.
*Styles.*—Three in number joined in a column.
*Length of styles.*—0.50 mm. in length.
*Style color.*—11A.
*Stigma.*—Bifid.

*Stigma dimensions.*—1 mm. in length and 1 mm. in width.

*Stigma color.*—11A.

*Ovary.*—No ovary observed to date.

Seed: No seed production has been observed to date.

We claim:

1. A new and distinct cultivar of *Euphorbia* plant named 'First Blush' as described and illustrated.

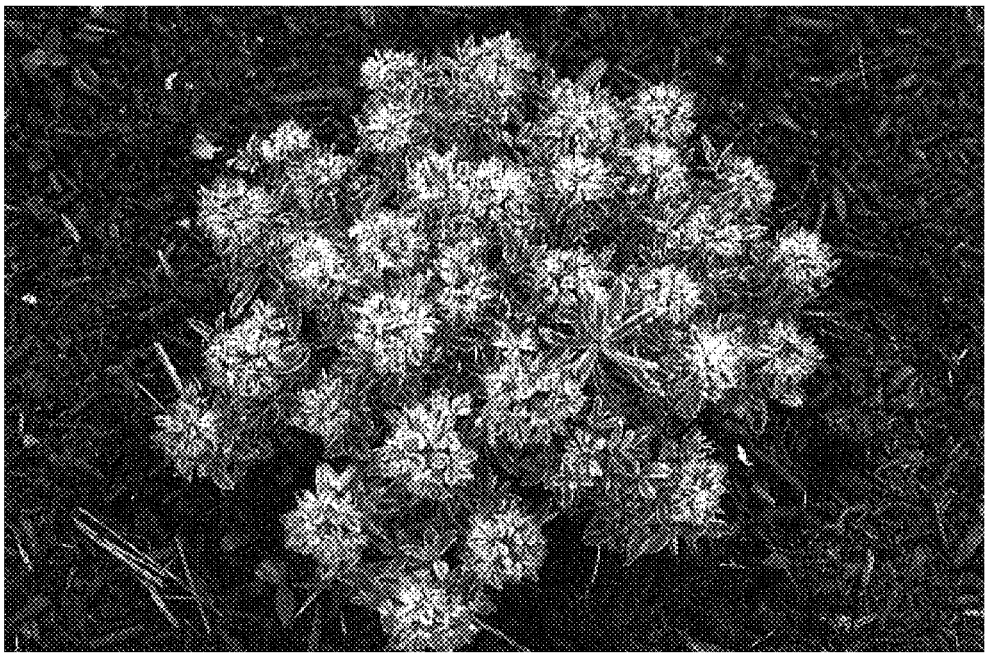

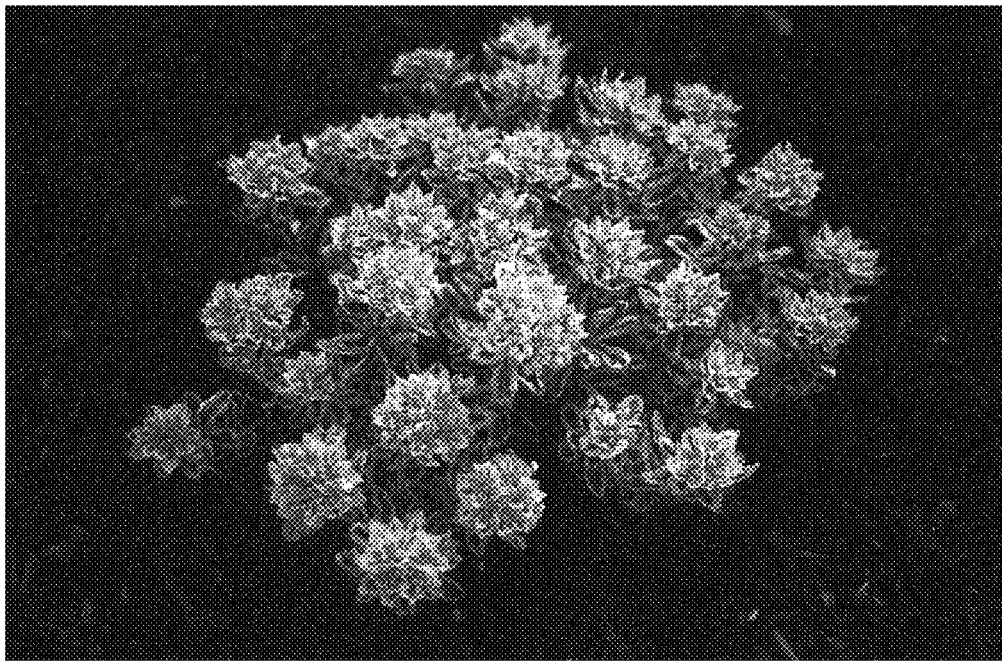

* * * * *